US00PP09997P

United States Patent [19]

Meilland

[11] Patent Number: Plant 9,997

[45] Date of Patent: Aug. 12, 1997

[54] HYBRID TEA ROSE PLANT NAMED 'MEICOFUM'

[75] Inventor: Alain A. Meilland, Antibes, France

[73] Assignee: The Conard-Pyle Company, West Grove, Pa.

[21] Appl. No.: 663,738

[22] Filed: Jun. 14, 1996

[51] Int. Cl.[6] ..... A01H 5/00

[52] U.S. Cl. ..... Plt./11

[58] Field of Search ..... Plt./11, 12

[56] References Cited

U.S. PATENT DOCUMENTS

P.P. 4,798 1/1982 Kordes ..... Plt./11

P.P. 8,414 10/1993 Winchell ..... Plt./11

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which abundantly forms attractive long-lasting bicolored blossoms that are reddish orange on the upper surface and creamy yellow on the under surface. The plant exhibits an erect growth habit and moderately strong vegetation. The new variety exhibits good disease resistance and is particularly well suited for cut flower production under greenhouse growing conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Krimony' variety (U.S. Plant Pat. No. 8,845). The male parent (i.e., the pollen parent) was the 'Mme. A. Meilland' variety (U.S. Plant Pat. No. 591). The 'Mme. A. Meilland' variety commonly is known as the 'Peace' variety. The parentage of the new variety can be summarized as follows:

'Krimony'×'Mme. A. Meilland'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms attractive long-lasting bicolored blossoms that are reddish orange on the upper surface and creamy yellow on the under surface,
(b) exhibits an erect growth habit,
(c) is well suited for cut flower production under greenhouse growing conditions, and
(d) exhibits good disease resistance.

The new variety well meets the needs of the horticultural industry and is particularly well suited for the commercial production of cut flowers while growing indoors.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meicofum' variety, and is being marketed under the Leonidas trademark.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouses at Le Cannet des Maures, Var, France.

DETAILED DESCRIPTION

Figures 1, 2, 3, 4, 5, 6, 7, 8, 9, 10, 11, 12, 13, 14:
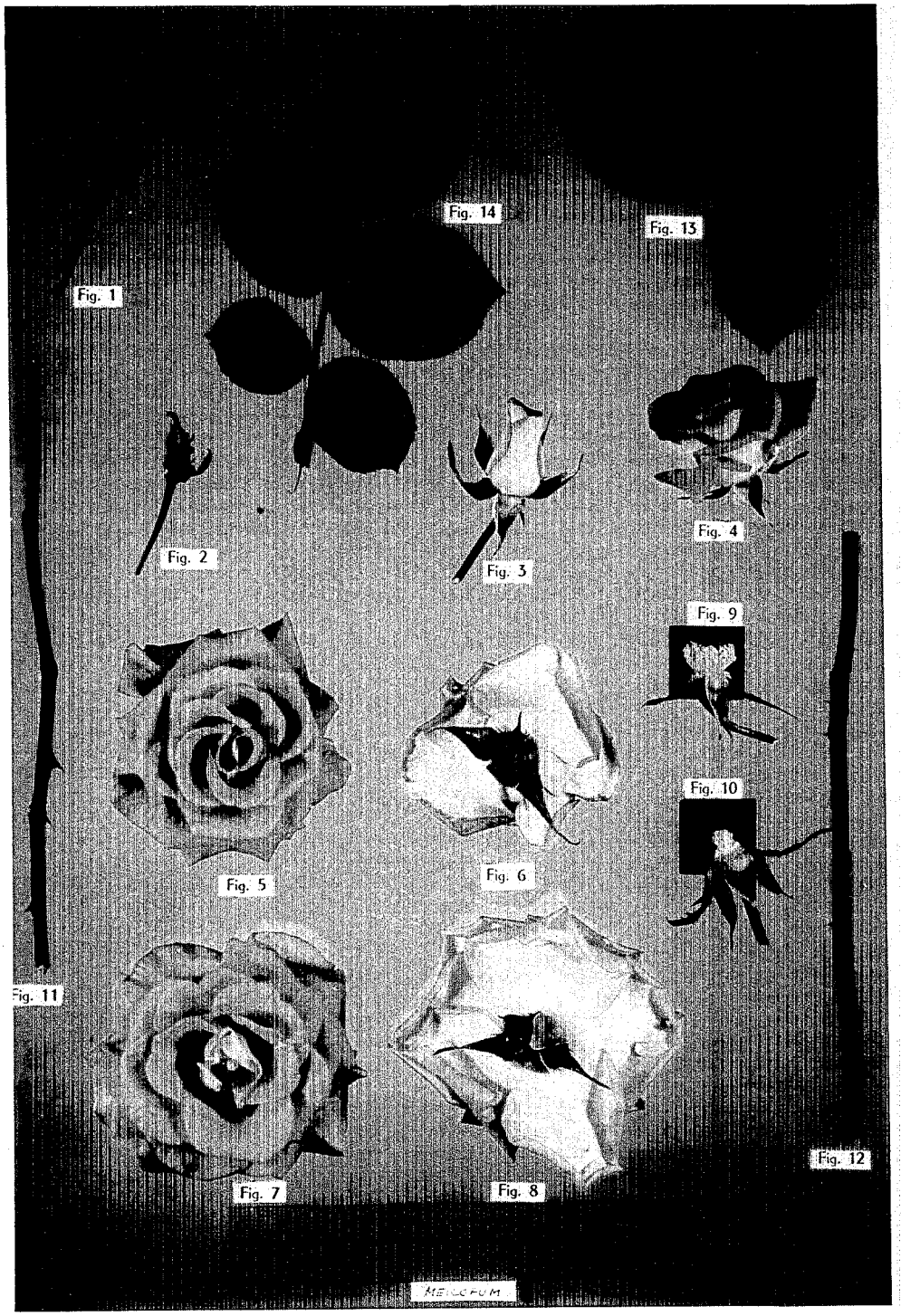
FIG. 1 illustrates a specimen of a young shoot.
FIG. 2 illustrates a specimen of a floral bud before the opening of the sepals.
FIG. 3 illustrates a specimen of a floral bud at the opening of the petals.
FIG. 4 illustrates a specimen of a flower in the course of opening.
FIG. 5 illustrates a specimen of an open flower — plan view — obverse.
FIG. 6 illustrates a specimen of an open flower — plan view — reverse.
FIG. 7 illustrates a specimen of a fully open flower — plan view — obverse.
FIG. 8 illustrates a specimen of a fully open flower — plan view — reverse.
FIG. 9 illustrates a specimen of a floral receptacle showing the arrangement of the stamens and pistils.
FIG. 10 illustrates a specimen of a floral receptacle showing the arrangement of the pistils (stamens removed)
FIG. 11 illustrates a specimen of a flowering stem.
FIG. 12 illustrates a specimen of a main branch.
FIG. 13 illustrates a specimen of a leaf with three leaflets — plan view — upper surface.
FIG. 14 illustrates a specimen of a leaf with five leaflets — plan view — under surface.

The chart used in the identification of the colors is that of The Royal Horticultural Society (R.H.S. Clour Chart). The description is based on the observation during November of two-year-old plants while budded on *Rosa indica* understock and growing in greenhouses at Le Cannet des Maures, Var, France. The coloration in common terms precedes reference to the chart.

Class: Hybrid Tea.

Plant:

*Height.*—When plants are pruned to a height of 0.85 m., floral stems of approximately 50 to 70 cm. in length commonly are formed.

*Habit.*—Erect.

Branches:

*Color.*—Young stems: light green, Green Group 139C and lightly suffused with reddish brown. Adult wood: medium green, Green Group 137D.

*Thorns.*—Size: medium. Quantity: moderately numerous. Color: greenish-reddish on young stems and greenish changing to tan on adult wood (as illustrated).

Leaves:

*Stipules.*—Adnate, pectinate, narrow and linear.

*Petioles.*—Upper surface: striped reddish brown on young foliage and medium green on adult foliage and somewhat glandular. Under surface: light green and rarely bear small thorns.

*Leaflets.*—Number: commonly 3, 5 (most often), and 7. Shape: oval. Serration: single and regular. Texture: consistent. General appearance: dense, and semi-glossy. Color (young foliage): Upper surface: bronze green, Yellow-Green Group 146A, and suffused with reddish-brown coloration. Under surface: light green, Greyed-Green Group 191B, and suffused with reddish-brown. Color (adult foliage): Upper surface: medium green, Green Group 137A. Under surface: light green, Green Group 138B.

Inflorescence:

*Number of flowers.*—Usually one flower per stem.

*Peduncle.*—Light green in coloration and smooth. The length commonly is approximately 12 to 13 cm. on average.

*Sepals.*—Upper surface: tomentose, and greenish in coloration. Under surface: light green in coloration and commonly with a few extensions (as illustrated).

*Buds.*—Shape: conical. Size: medium. Length: approximately 4 cm. on average. Color upon opening: Upper surface: Currant Red, Red Group 46A. Under surface: light Mustard Yellow, Greyed-Yellow Green 162A, with a small edge of Currant Red, Red Group 46A.

*Flower.*—Shape: cup-shaped with a high center. Diameter: approximately 12 to 14 cm. on average. Color (when opening begins): Upper surface: dark red, Greyed-Purple Group 185A. Under surface: Brick Orange, Greyed-Orange Group 169B, with a small edge of deep red, Greyed-Purple Group 185A. Color (when blooming): Upper surface: Majolica Yellow, Greyed-Orange Group 170A. Under surface: Chrome Yellow, Yellow-Orange Group 15D. Color (at end of opening): Upper surface: Majolica Yellow, Greyed-Orange Group 170A. Under surface: Chrome Yellow, Yellow-Orange Group 15C. Fragrance: none. Lasting quality: long. When cut and placed in a vase, the blossoms commonly last approximately 7 to 9 days. The blossom life is influenced by the environmental conditions that are encountered. Petal shape: rounded with reflexed edges. Petal drop: good. Stamen number: approximately 82 to 90 on average. Anthers: normal and ochre in coloration. Filaments: canary yellow in coloration. Pistils: approximately 75 to 80 on average. Stigmas: ochre in coloration. Styles: canary yellow in coloration. Receptacle: light green in coloration, smooth, and in longitudinal section in the shape of a funnel.

Development:

*Vegetation.*—Moderatley strong.

*Blooming.*—Normal abundance.

*Resistance to diseases.*—Good.

I claim:

1. A new and distinct variety of Hybrid Tea rose plant characterized by the following combination of characteristics:

(a) forms attractive long-lasting bicolored blossoms that are reddish orange on the upper surface and creamy yellow on the under surface,
(b) exhibits an erect growth habit,
(c) is well suited for cut flower production under greenhouse growing conditions, and
(d) exhibits good disease resistance;

substantially as herein shown and described.

* * * * *